US011933691B2

(12) United States Patent
Zhang et al.

(10) Patent No.: US 11,933,691 B2
(45) Date of Patent: Mar. 19, 2024

(54) CO₂ STORAGE STATE NETWORKING MONITORING DEVICE, SYSTEM AND METHOD WITH MULTI-INFORMATION FUSION

(71) Applicant: Institute of Geology and Geophysics, Chinese Academy of Sciences, Beijing (CN)

(72) Inventors: Wang Zhang, Beijing (CN); Fei Tian, Beijing (CN); Yongjian Zhou, Beijing (CN); Wenhao Zheng, Beijing (CN); Yongwen Yang, Beijing (CN)

(73) Assignee: Institute of Geology and Geophysics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/878,364

(22) Filed: Aug. 1, 2022

(65) Prior Publication Data

US 2023/0184614 A1 Jun. 15, 2023

(30) Foreign Application Priority Data

Dec. 15, 2021 (CN) .......................... 202111527288.4

(51) Int. Cl.
*G01D 21/02* (2006.01)
*G01M 3/04* (2006.01)
(Continued)

(52) U.S. Cl.
CPC ............ *G01M 3/04* (2013.01); *G01N 33/004* (2013.01); *G01V 3/02* (2013.01); *G01D 21/02* (2013.01)

(58) Field of Classification Search
CPC ......... G01V 3/02; G01N 33/004; G01M 3/04; G01D 21/00; G01D 21/02
See application file for complete search history.

(56) References Cited

U.S. PATENT DOCUMENTS

| 11,414,986 B1* | 8/2022 | Cha ....................... E21B 47/017 |
| 2010/0257926 A1* | 10/2010 | Yamate .................. E21B 49/08 |
| | | 73/152.23 |

(Continued)

FOREIGN PATENT DOCUMENTS

| CN | 106324187 A | 1/2017 |
| CN | 111323817 A | 6/2020 |
| CN | 111337980 A | 6/2020 |

*Primary Examiner* — Jeff W Natalini
(74) *Attorney, Agent, or Firm* — Nitin Kaushik

(57) ABSTRACT

The present invention belongs to the field of environment monitoring, particularly relates to a $CO_2$ storage state networking monitoring device, system and method with multi-information fusion. The present invention comprises: obtaining orientation electrical signal data and real-time pressure signals, analyzing a fluid flowing state at a view of a pressure sensor through the real-time pressure signals, and obtaining a $CO_2$ flowing state through the orientation electrical signal data; and obtaining a $CO_2$ regional storage state by combining an orientation $CO_2$ content, a $CO_2$ flowing state and the fluid flowing condition at the view of the pressure sensor. By combining accurate short-range $CO_2$ boundary monitoring of orientation electrodes with long-range monitoring of pressure sensors to achieve a wide range of $CO_2$ flowing state monitoring, the present invention can observe more data with higher reliability and effectively aims at the problem of strong inter-well heterogeneity.

8 Claims, 9 Drawing Sheets

(51) Int. Cl.
*G01N 33/00* (2006.01)
*G01V 3/02* (2006.01)

(56) References Cited

U.S. PATENT DOCUMENTS

2014/0091803 A1* 4/2014 Dodds ...................... G01V 3/18
 405/129.5
2016/0161630 A1* 6/2016 Badri .................... E21B 49/008
 324/303
2022/0341295 A1* 10/2022 Chen ....................... H02J 50/20

* cited by examiner

$CO_2$ STORAGE STATE NETWORKING MONITORING DEVICE, SYSTEM AND METHOD WITH MULTI-INFORMATION FUSION

CROSS-REFERENCE TO RELATED APPLICATIONS

The application claims priority to Chinese patent application No. 202111527288.4, filed on Dec. 15, 2021, the entire contents of which are incorporated herein by reference.

TECHNICAL FIELD

The present invention belongs to the field of environment monitoring and particularly relates to a $CO_2$ storage state networking monitoring device, system and method with multi-information fusion.

BACKGROUND

In recent years, there are a lot of researches on capturing, using and sequestering $CO_2$ going on around the world. A great quantity of $CO_2$ captured in the industrial process is injected into a rock stratum deep in the earth and then are permanently removed from the atmosphere, and thus an emission reduction target of $CO_2$ in global atmosphere is achieved. By injecting $CO_2$ into a subsurface reservoir, the recovery efficiency may be increased, and the purpose of permanently storing $CO_2$ may further be achieved. Although the $CO_2$ geological storage technology has become mature, more and more evidences show that the safety of $CO_2$ geological storage is the technical bottleneck restricting large-scale popularization and application of the $CO_2$ geological storage technology. How to effectively prevent, monitor and control leakage of $CO_2$ and ensure the safety of $CO_2$ storage has become an important content of research on the $CO_2$ storage technology and has been given more and more attention.

One of focuses on the safety of $CO_2$ geological storage is monitoring on plume motion and possible leakage of $CO_2$. At present, the mainstream $CO_2$ monitoring technology comprises delay earthquakes (also called 4D earthquake), repeated electromagnetic surveying (4D EM/CSEM), microearthquakes and GPS monitoring. Earthquakes have been determined as a method with high cost and high returns, whereas 4D EM is considered as a $CO_2$ monitoring technology with low cost and high returns. In fact, direction observation on geological bodies storing $CO_2$ can obtain more data with higher reliability; however, the cost of drilling a lot of monitoring wells is very high, and the problem of strong inter-well heterogeneity of the geological bodies cannot be well solved always.

SUMMARY

In order to solve the above problems in the prior art, i.e. the problems that the cost is relatively high, and resistance space distribution and changes of strong-heterogeneity geological bodies cannot be dealt with of the existing $CO_2$ geological storage technology and the problem that the monitoring continuity is easily poor due to improvement on detecting precision in multi-directional $CO_2$ detection, the present invention provides a $CO_2$ storage state networking monitoring device with multi-information fusion, comprising a plurality of dispersed multi-information $CO_2$ underground monitoring devices and a ground monitoring device;

each multi-information $CO_2$ underground monitoring device comprises a cable mounted at the external of a non-conductive sleeve and a preset number of multi-information sensor arrays in preset orientations; and each sensor terminal of each multi-information sensor array at least comprises orientation electrodes and a pressure sensor and is connected with the cable;

wherein each multi-information sensor array comprises a preset number of orientation electrodes which are in one orientation and vertically inserted into the non-conductive sleeve; and the pressure sensor is a multidirectional sensor;

the ground monitoring device comprises a current source, an emitting apparatus, a downhole sensor detection module and a computer center control.

In another aspect of the present invention, provided is a $CO_2$ storage state networking monitoring system with multi-information fusion, applied to the above $CO_2$ storage state networking monitoring device with multi-information fusion. The system comprises: an orientation electrical signal obtaining unit, an orientation pressure signal obtaining unit, a flowing state analyzing unit, a flowing component analyzing unit, a regional $CO_2$ state analyzing unit and a continuous monitoring unit;

the orientation electrical signal obtaining unit is configured in such a way that a single multi-information sensor array is selected through the ground monitoring device, an emitter electrode and a receiver electrode are provided, a detection current in a preset waveform is emitted by the emitter electrode, the lost detection current is received by the receiver electrode, a potential difference between the electrodes is obtained, the potential difference between the electrodes is measured by selecting another combination of the emitter electrode and the receiver electrode, all the potential differences between the electrodes in one orientation form orientation electrical signal data, electrical signal data in the another orientation is obtained by selecting another orientation electrode array until collection of all the electrical signal data in all orientations of single monitoring device is completed, and all the orientation electrical signal data is combined into single-monitoring-device electrical signal data;

the orientation pressure signal obtaining unit is configured to continuously obtain real-time pressure signals through all multidirectional pressure sensors;

the flowing state analyzing unit is configured in such a way that the single-monitoring-device electrical signal data and the real-time pressure signals are obtained by the ground monitoring device, and the real-time pressure signals are counted into a pressure signal set;

a latest pressure signal segment with a preset duration is intercepted, and the fluid flowing condition at the view of the pressure sensor is analyzed;

the single-monitoring-device electrical signal data is inverted to obtain resistivity grid distribution images in all the orientations;

the flowing component analyzing unit is configured to calculate orientation $CO_2$ distribution and a $CO_2$ flowing state at an electrode view based on the resistivity grid distribution images;

the regional $CO_2$ state analyzing unit is configured to summarize the $CO_2$ flowing states at the electrode view and the $CO_2$ flowing states at the pressure view of all the $CO_2$ underground monitoring apparatuses to obtain a $CO_2$ flowing state between devices and obtain the $CO_2$ regional storage state based on the $CO_2$ flowing state between device;

the continuous monitoring unit is configured to repeat functions of the orientation electrical signal obtaining unit, the orientation pressure signal obtaining unit, the flowing state analyzing unit, the flowing component analyzing unit and the regional $CO_2$ state analyzing unit and continuously monitor the $CO_2$ flowing state in the region underground.

In some preferred embodiments, an orientation electrical signal obtaining unit is provided. A running mode of the orientation electrical signal obtaining unit comprises a single-electrode emitting measurement mode, a symmetric-electrode emitting measurement mode, a remote detection mode and an attenuation-lowering remote detection mode.

In some preferred embodiments, a $CO_2$ flowing state at a pressure view is obtained based on orientation $CO_2$ distribution and a fluid flowing condition at a view of a pressure sensor.

Specifically, the fluid flowing condition at the view of the pressure sensor in a detection range from a corresponding depth horizontal direction to a wellbore is obtained through a latest pressure signal segment; and the $CO_2$ flowing state at the pressure view is obtained based on the fluid flowing condition at the view of the pressure sensor and an orientation $CO_2$ distribution image.

In some preferred embodiments, the obtaining the fluid flowing condition at the view of the pressure sensor in the detection range from the corresponding depth horizontal direction to the wellbore through the latest pressure signal segment comprises: drawing a double logarithmic curve based on the obtained latest pressure signal segment, selecting a correct model according to the geological conditions, and making typical curve fitting to obtain the fluid flowing condition at the view of the pressure sensor.

In some preferred embodiments, the obtaining the $CO_2$ flowing state at the pressure view based on the fluid flowing condition at the view of the pressure sensor and the orientation $CO_2$ distribution image further comprises: calculating an estimated pressure variation quantity of $CO_2$ entering a corresponding detection region based on different rock strata where the pressure sensors are located and different geological conditions; and judging whether there is a $CO_2$ longitudinal flow or not by comparing the latest pressure signal segment with the estimated pressure variation quantity.

In some preferred embodiments, the obtaining a $CO_2$ regional storage state based on the $CO_2$ flowing state and a $CO_2$ flowing state between devices is specifically as follows:

the $CO_2$ flowing state between the devices is analyzed; and if the $CO_2$ flowing state of a certain monitoring device represents that there is $CO_2$ leakage in the detection region, orientation pressure may be reduced in probing stations in upstream and downstream directions of the detection region, and the $CO_2$ flowing state of the probing station in each direction may display that $CO_2$ moves in a leakage direction.

In the third aspect of the present invention, provided is a $CO_2$ storage state networking monitoring method with multi-information fusion. The method is applied to the above $CO_2$ storage state networking monitoring device with multi-information fusion;

step S100, selecting a single multi-information sensor array through the ground monitoring device, providing an emitter electrode and a receiver electrode, emitting a detection current in a preset waveform by the emitter electrode, receiving the lost detection current by the receiver electrode, obtaining a potential difference between the electrodes, measuring the potential difference between the electrodes by selecting another combination of the emitter electrode and the receiver electrode, enabling all the potential differences between the electrodes in one orientation to form orientation electrical signal data, obtaining electrical signal data in the another orientation by selecting another orientation electrode array until collection of all the electrical signal data in all orientations of single monitoring device is completed, and combining all the orientation electrical signal data into single-monitoring-device electrical signal data;

step S200, continuously obtaining real-time pressure signals through all multidirectional pressure sensors;

step S300, obtaining the single-monitoring-device electrical signal data and the real-time pressure signals by the ground monitoring device, and counting the real-time pressure signals into a pressure signal set;

intercepting a latest pressure signal segment with a preset duration, and analyzing the fluid flowing condition at the view of the pressure sensor;

inverting the single-monitoring-device electrical signal data to obtain resistivity grid distribution images in all the orientations;

step S400, calculating orientation $CO_2$ distribution and a $CO_2$ flowing state at an electrode view based on the resistivity grid distribution images;

obtaining the $CO_2$ flowing state at the pressure view based on the orientation $CO_2$ distribution and the fluid flowing condition at the view of the pressure sensor, and obtaining the $CO_2$ regional storage state based on the $CO_2$ flowing state and the $CO_2$ flowing state between the devices;

step S500, summarizing the $CO_2$ flowing states at the electrode view and the $CO_2$ flowing states at the pressure view of all the $CO_2$ underground monitoring apparatuses to obtain a $CO_2$ flowing state between devices;

obtaining the $CO_2$ regional storage state based on the $CO_2$ flowing state between devices;

step S600, repeating the steps from S100 to S500, and continuously monitoring the $CO_2$ flowing state in the region underground.

In the fourth aspect of the present invention, provided is an electronic device, comprising at least one processor and a memory in communication connection with the at least one processor, wherein the memory stores instructions which may be executed by the processor, and the instructions are used for being executed by the processor so as to implement the $CO_2$ storage state networking monitoring method with multi-information fusion.

In the fifth aspect of the present invention, provided is a computer center control readable storage medium, wherein the computer center control instructions arc executed by a computer center control to implement the $CO_2$ storage state networking monitoring method with multi-information fusion.

The present invention has the beneficial effects that:
(1) By combining accurate middle-short-range $CO_2$ boundary monitoring of orientation electrodes with long-range monitoring of pressure sensors to achieve a wide range of $CO_2$ flowing state monitoring, the present invention can observe more data with higher reliability and effectively aims at the problem of strong inter-well heterogeneity;
(2) The present invention supplements an interval of monitoring of the orientation electrodes with continuous monitoring of the pressure sensors and achieves continuous monitoring on underground stored $CO_2$;
(3) By using the pressure sensors, the present invention may achieve the effect of long-range monitoring and data interaction between the detection devices, and thus the monitoring accuracy is improved to avoid misjudgment;

(4) The present invention conducts complementary analysis by obtaining data of two different attributes of electricity and pressure at the same time and may further conduct analysis by singly using one attribute at the same time, so that the reliability of monitoring is improved.

DETAILED DESCRIPTION OF THE EMBODIMENTS

The present invention provides a $CO_2$ storage state networking monitoring device with multi-information fusion, comprising a plurality of dispersed multi-information $CO_2$ underground monitoring devices and a ground monitoring device.

Each multi-information $CO_2$ underground monitoring device comprises a cable mounted at the external of a non-conductive sleeve and a preset number of multi-information sensor arrays in preset orientations. Each sensor terminal of each multi-information sensor array at least comprises orientation electrodes and a pressure sensor and is connected with the cable.

Each multi-information sensor array comprises a preset number of orientation electrodes which are in one orientation and vertically inserted into the non-conductive sleeve; and each pressure sensor is a multidirectional sensor.

Figure 3:
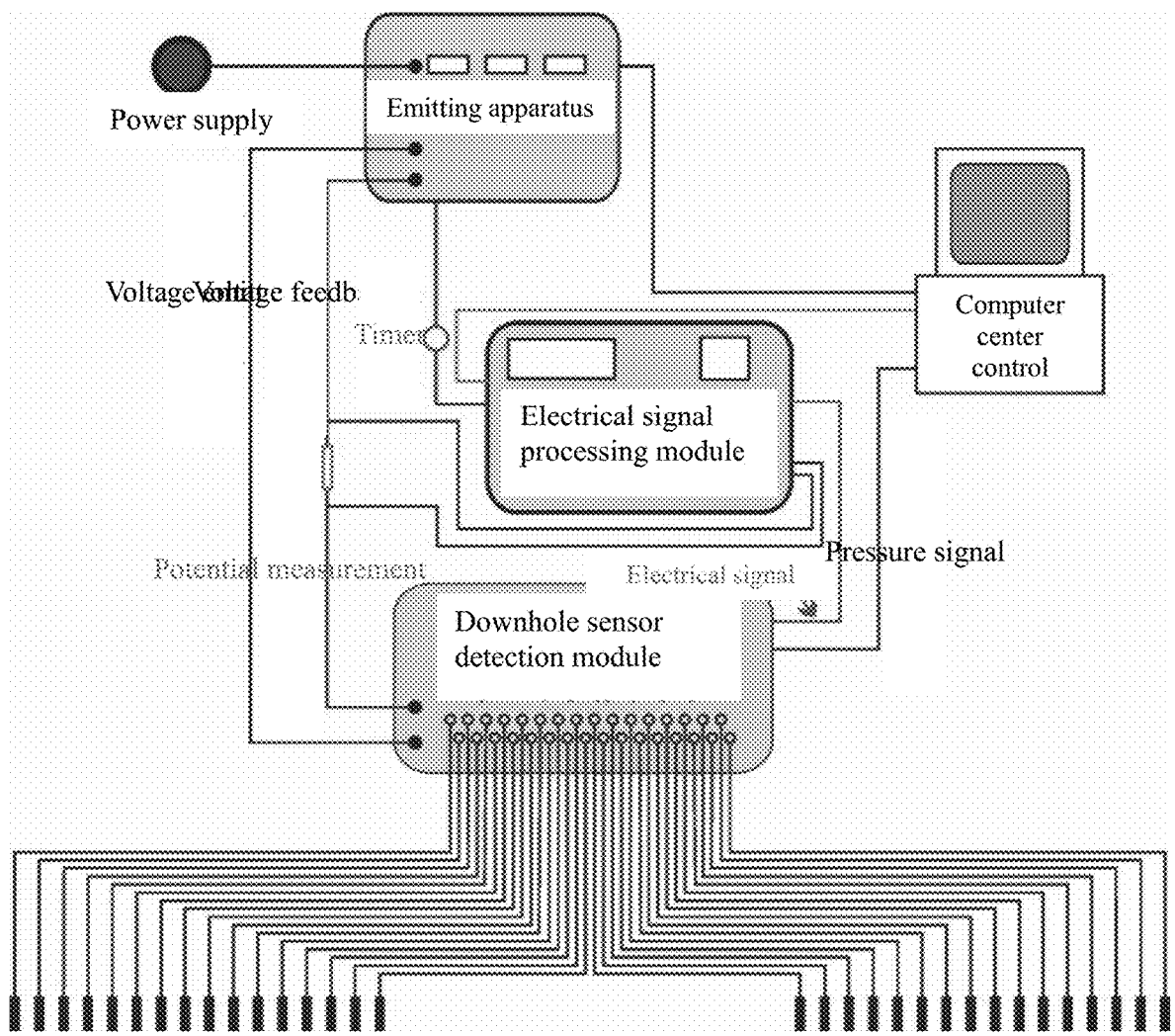
FIG. 3 is a principle diagram of a ground monitoring device in embodiments of the R) present invention.

As shown in FIG. 3, the ground monitoring device comprises a current source, an emitting apparatus, a downhole sensor detection module and a computer center control. A power supply is connected with the emitting apparatus, the emitting apparatus is connected with the downhole sensor detection module through a voltage emitting line and a voltage feedback line, the voltage feedback line is further connected with a potential measurement resistor, the two ends of the potential measurement resistor are connected with an electrical signal processing module, the electrical signal processing module is connected with the computer center control and the downhole sensor detection module at the same time and is connected with the emitting apparatus through a timer, and the downhole sensor detection module is additionally in direct connection with the computer center control and the electrical signal processing module.

The present invention provides a $CO_2$ storage state networking monitoring system with multi-information fusion, applied to the above $CO_2$ storage state networking monitoring device with multi-information fusion. The system comprises an orientation electrical signal obtaining unit, an orientation pressure signal obtaining unit, a flowing state analyzing unit, a flowing component analyzing unit, a regional $CO_2$ state analyzing unit and a continuous monitoring unit;

the orientation electrical signal obtaining unit is configured in such a way that a single multi-information sensor array is selected through the ground monitoring device, an emitter electrode and a receiver electrode arc provided, a detection current in a preset waveform is emitted by the emitter electrode, the lost detection current is received by the receiver electrode, a potential difference between the electrodes is obtained, the potential difference between the electrodes is measured by selecting another combination of the emitter electrode and the receiver electrode, all the potential differences between the electrodes in one orientation form orientation electrical signal data, electrical signal data in the another orientation is obtained by selecting another orientation electrode array until collection of all the electrical signal data in all orientations of single monitoring device is completed, and all the orientation electrical signal data is combined into single-monitoring-device electrical signal data;

the orientation pressure signal obtaining unit is configured to continuously obtain real-time pressure signals through all multidirectional pressure sensors;

the flowing state analyzing unit is configured in such a way that the single-monitoring-device electrical signal data and the real-time pressure signals are obtained by the ground monitoring device, and the real-time pressure signals arc counted into a pressure signal set;

a latest pressure signal segment with a preset duration is intercepted, and the fluid flowing condition at the view of the pressure sensor is analyzed;

the single-monitoring-device electrical signal data is inverted to obtain resistivity grid distribution images in all the orientations;

the flowing component analyzing unit is configured to calculate orientation $CO_2$ distribution and a $CO_2$ flowing state at an electrode view based on the resistivity grid distribution images;

the regional $CO_2$ state analyzing unit is configured to summarize the $CO_2$ flowing states at the electrode view and the $CO_2$ flowing states at the pressure view of all the $CO_2$ underground monitoring apparatuses to obtain a $CO_2$ flowing state between devices and obtain the $CO_2$ regional storage state based on the $CO_2$ flowing state between device;

the continuous monitoring unit is configured to repeat functions of the orientation electrical signal obtaining unit, the orientation pressure signal obtaining unit, the flowing state analyzing unit, the flowing component analyzing unit and the regional $CO_2$ state analyzing unit and continuously monitor the $CO_2$ flowing state in the region underground.

by combining accurate middle-short-range $CO_2$ boundary monitoring of the orientation electrodes with long-range monitoring of the pressure sensors to achieve a wide range of $CO_2$ flowing state monitoring, more data with higher reliability can be observed, and the problem of strong inter-well heterogeneity is effectively aimed at.

Figure 1:
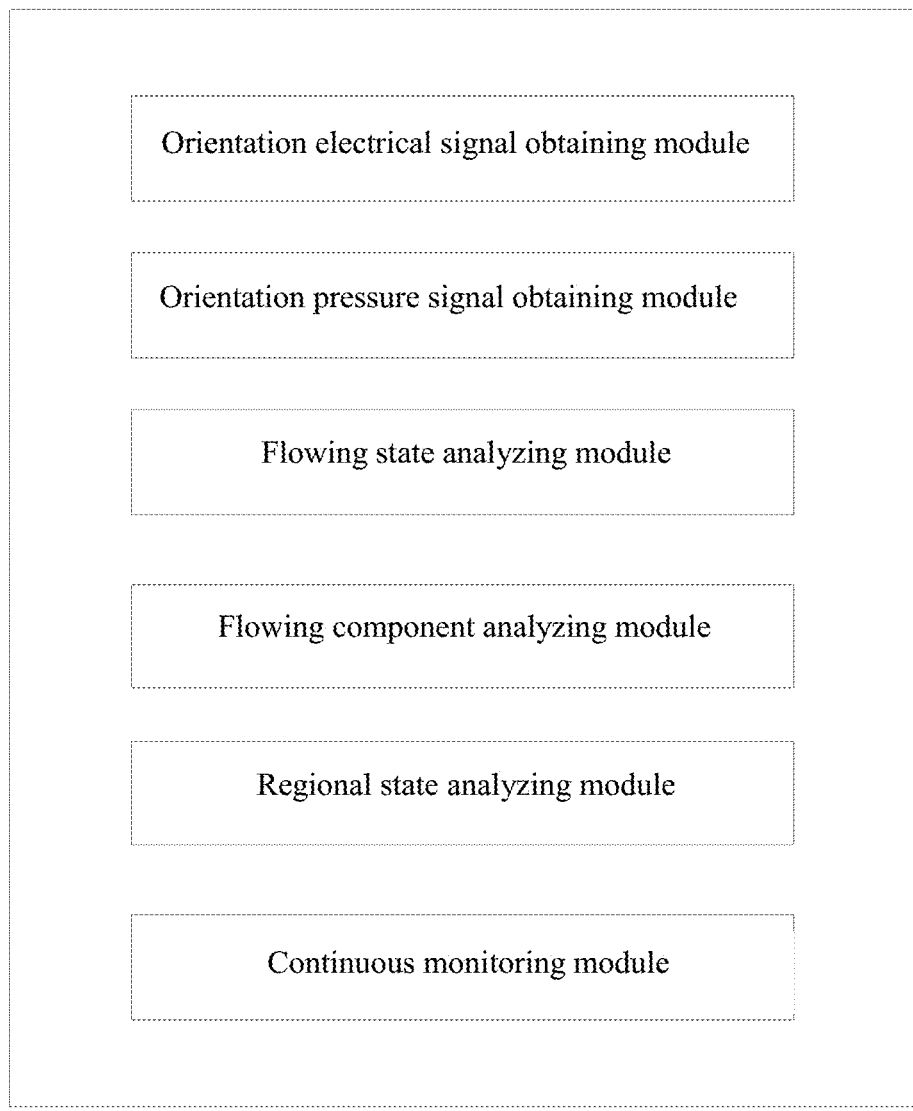
FIG. 1 is a structural block diagram of a $CO_2$ storage state networking monitoring system with multi-information fusion according to embodiments of the present invention.

In order to more clearly describe the $CO_2$ storage state networking monitoring device with multi-information fusion of the present invention, various steps in the embodiments of the present invention are described in detail in combination with FIG. 1 below.

Figure 4:
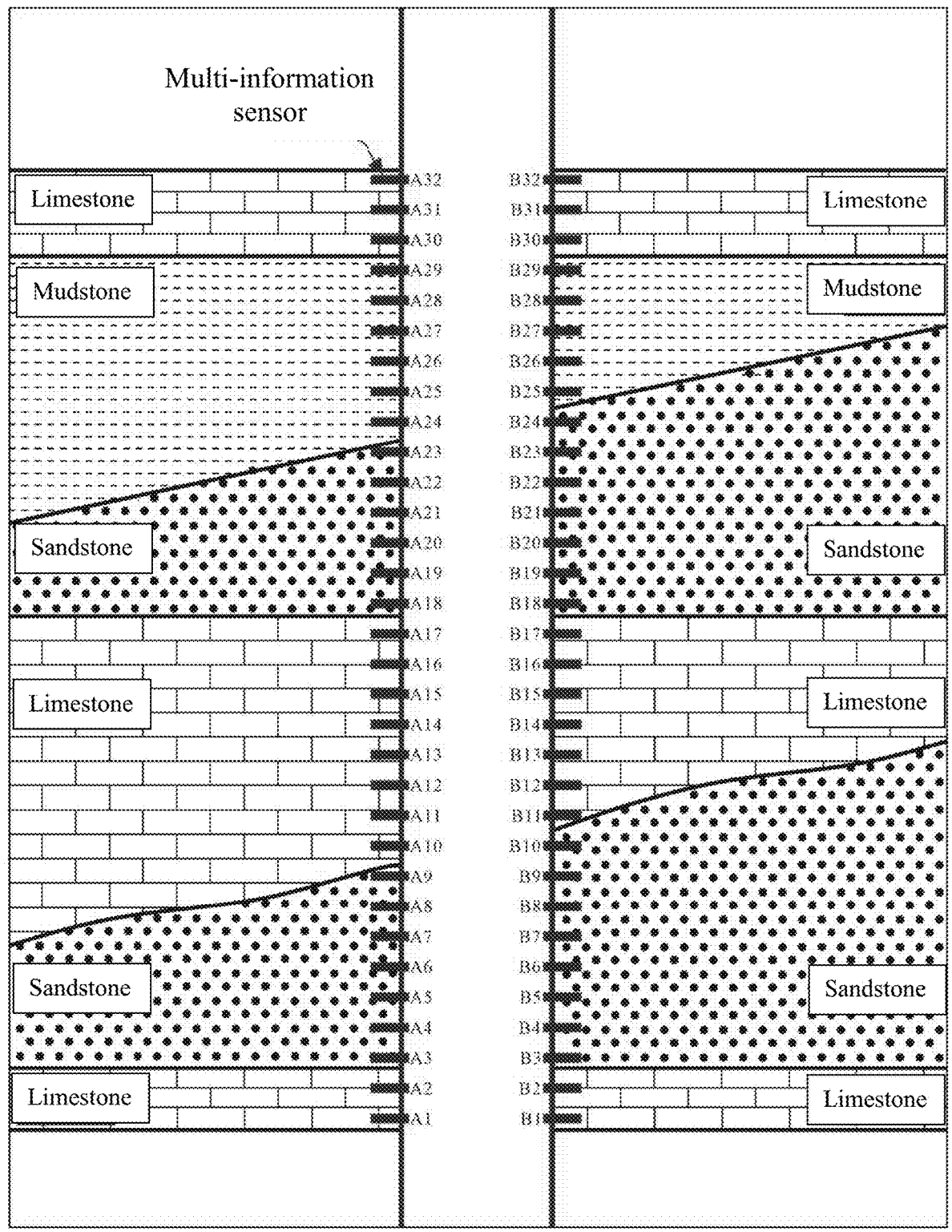
FIG. 4 is a principle diagram of disposing a multi-information $CO_2$ underground monitoring device underground in embodiments of the present invention.

A $CO_2$ storage state networking monitoring system with multi-information fusion of the first embodiment of the present invention is applied to the $CO_2$ storage state networking monitoring device with multi-information fusion and comprises a plurality of dispersed multi-information $CO_2$ underground monitoring devices and a ground monitoring device. The multi-information $CO_2$ underground monitoring devices are subjected to traditional oilfield type grouting at a plurality of testing wells to enable all cables and multi-information sensor arrays to be buried into cement at the externals of the corresponding sleeve, as shown in FIG. 4.

The monitoring system comprises an orientation electrical signal obtaining unit, an orientation pressure signal obtaining unit, a flowing state analyzing unit, a flowing component analyzing unit, a regional $CO_2$ state analyzing unit and a continuous monitoring unit. Various functional units are described in detail as follows:

The orientation electrical signal obtaining unit is configured in such a way that a single multi-information sensor array through the ground monitoring device is selected, an emitter electrode and a receiver electrode is provided, a detection current in a preset waveform is emitted by the emitter electrode, the lost detection current is received by the receiver electrode, a potential difference between the electrodes is obtained, the potential difference between the electrodes is measured by selecting another combination of the emitter electrode and the receiver electrode, all the potential differences between the electrodes in one orientation form orientation electrical signal data, electrical signal data in the another orientation is obtained by selecting another orientation electrode array until collection of all the electrical signal data in all orientations of single monitoring device is completed, and all the orientation electrical signal data is combined into single-monitoring-device electrical signal data.

Figure 5:
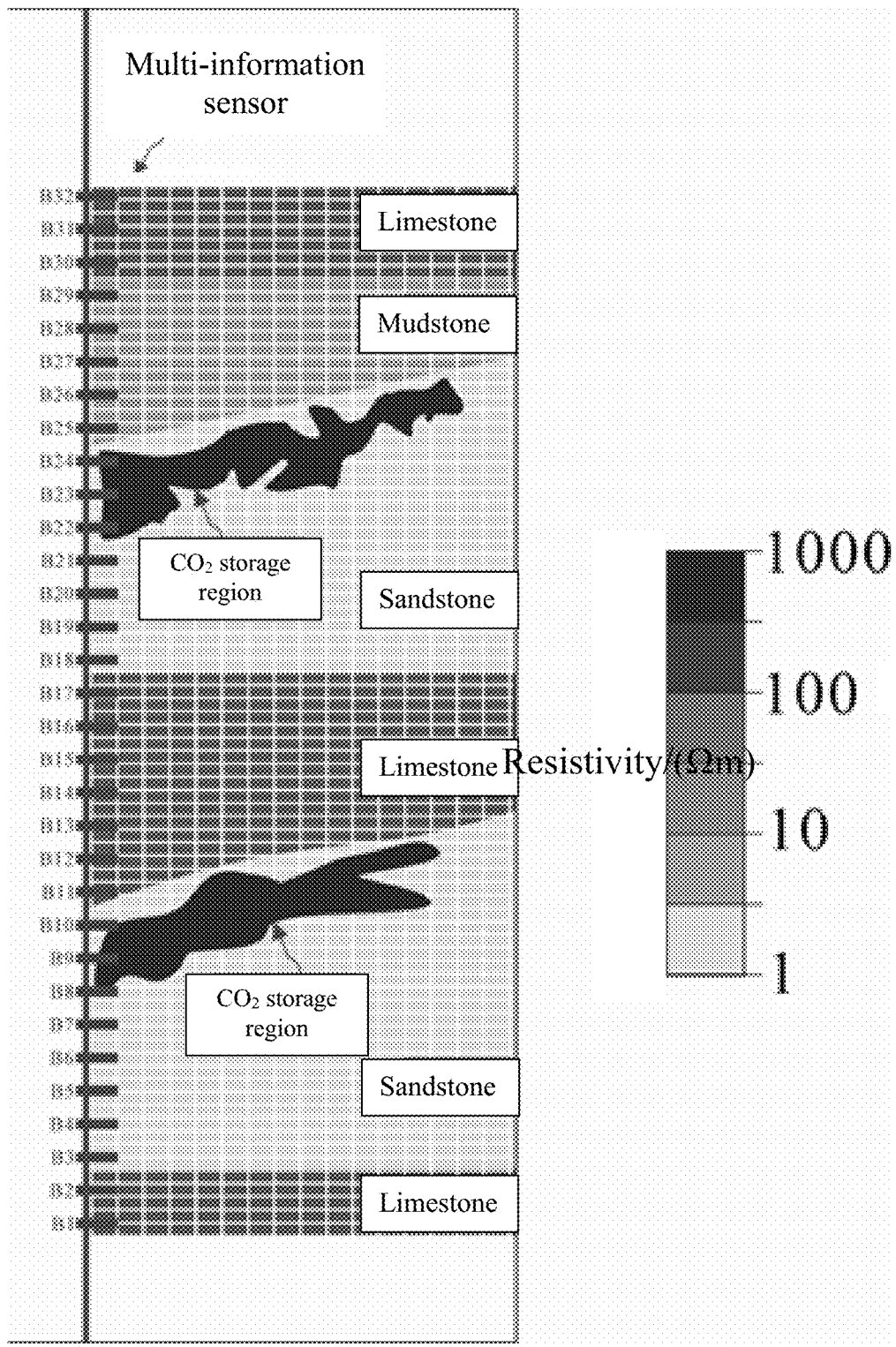
FIG. 5 is schematic diagram of a resistivity grid distribution image obtained by voltage data set inversion in one orientation in embodiments of the present invention.
Figure 6:
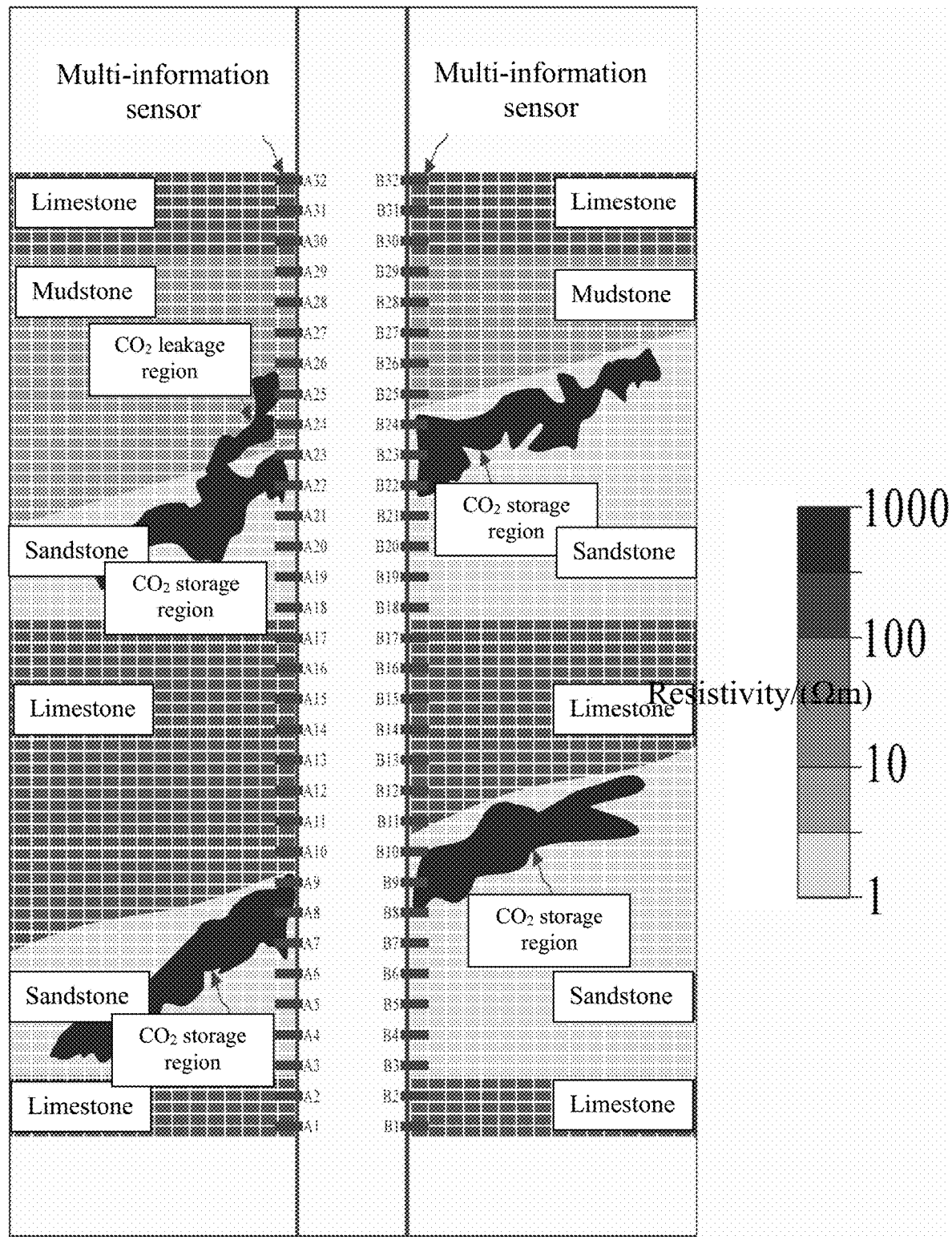
FIG. 6 is a resistivity grid distribution diagram in embodiments of the present invention.
Figure 7:
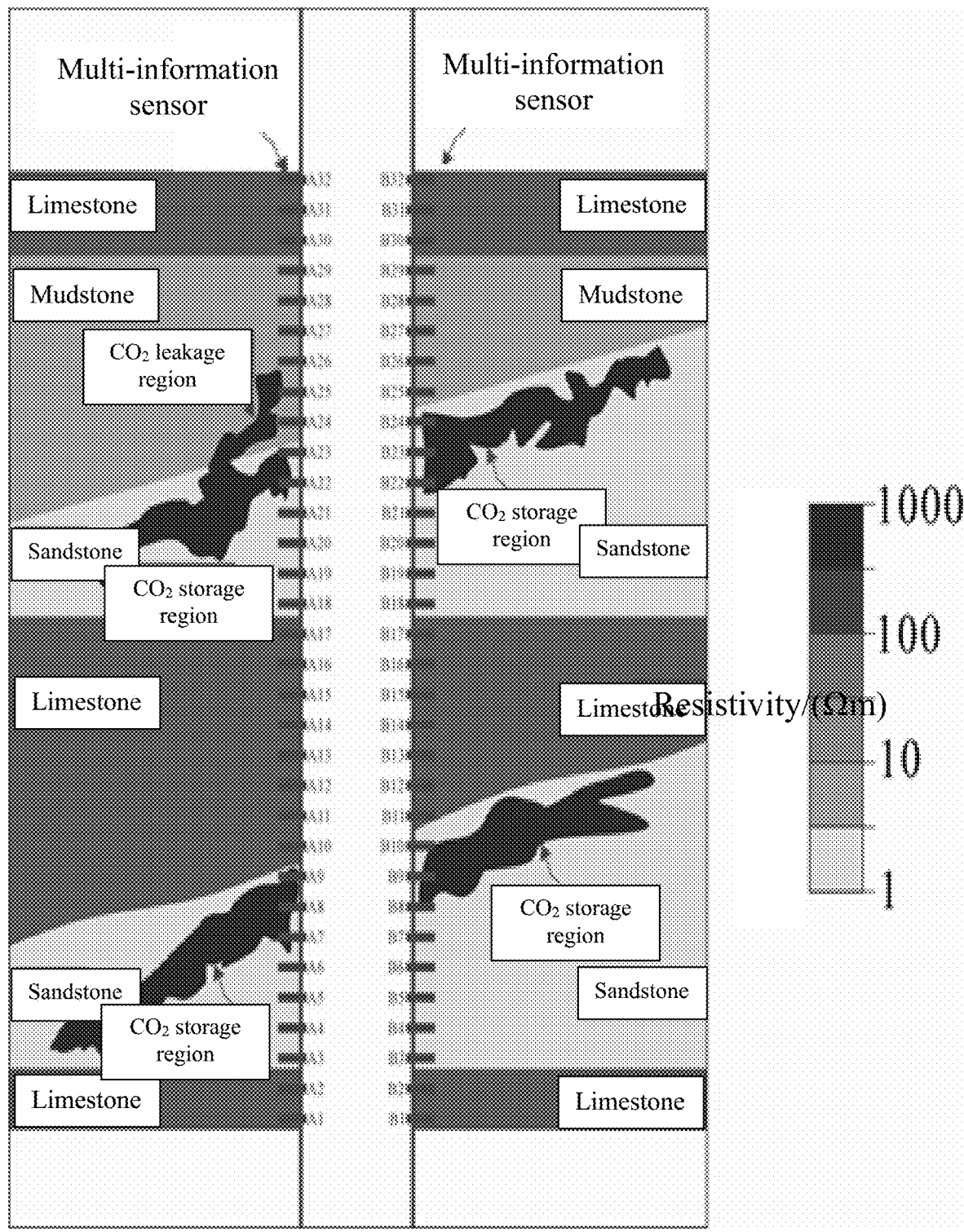
FIG. 7 is schematic diagram of a $CO_2$ whole distribution state of a single monitoring apparatus in embodiments of the present invention.

In this embodiment, for the orientation electrical signal obtaining unit, a running mode comprises: a single-electrode emitting measurement mode, a symmetric-electrode emitting measurement mode, a remote detection mode and an attenuation-lowering remote detection mode;

the single-electrode emitting measurement mode is specifically as follows:
any one metal electrode is selected as the emitter electrode, the other n−1 electrodes serve as the receiver electrodes, the potential difference between the electrodes in each group of emitter electrode-receiver electrodes is recorded as a potential difference for single-electrode emitting measurement;
another metal electrode, never being selected, is selected as the emitter electrode, the potential difference between the electrodes in each group of emitter electrode-receiver electrodes is measured until all the metal electrodes have been selected as the emitter electrodes, and the potential difference for single-electrode emitting measurement is recorded;
the symmetric-electrode emitting measurement mode is specifically as follows:
the center of a length of each non-conductive sleeve is selected as a symmetric axis, and the metal electrodes, equally distant from the symmetric axis, serve as a metal electrode pair;
any one metal electrode pair is selected as the emitter electrode pair, the other n−2 electrodes serve as the receiver electrodes, the potential difference between the electrodes in each group of the emitter electrode pair-receiver electrodes is recorded as a potential difference for symmetric-electrode emitting measurement;
another metal electrode pair, never being selected, is selected as the emitter electrode, the potential difference between the electrodes in each group of emitter electrode-receiver electrodes is measured until all the metal electrode pairs have been selected as the emitter electrode pairs, and the potential difference for symmetric-electrode emitting measurement is recorded;
the remote detection mode is specifically as follows:
two electrodes A and B at a preset interval of k electrodes are selected as high-voltage emitter electrodes, wherein k is even;
two electrodes C and D in the middle between the electrodes A and B are selected as high-voltage emitter electrodes, and A, B, C and D form a high-voltage emitter electrode group;
a detection current at high voltage is emitted by the high-voltage emitter electrodes, the other n−4 electrodes serve as receiver electrodes, and a potential different between each group of high-voltage emitter electrode group-receiver electrodes is recorded as a potential different for remote detection;
another metal electrode combination, never being selected, is selected as a high-voltage emitter electrode group, the potential different between each group of high-voltage emitter electrode group-receiver electrodes is measured until all possible high-voltage metal electrode combinations are selected, and the potential different for remote detection is recorded;
the attenuation-lowering remote detection mode is specifically as follows:
two electrodes E and F at a preset interval of q electrodes are selected as low-voltage emitter electrodes, wherein q is even;
two electrodes G and H in the middle between the electrodes E and F are selected as high-voltage emitter electrodes, and E, F, G and H serve as an attenuation-lowering remote detection emitter electrode group;
a detection current at low voltage is emitted by the low-voltage emitter electrodes, a detection current at high voltage is emitted by the high-voltage emitter electrodes, at this time, a potential different between the two electrodes, close to the low-voltage emitter electrodes between high-voltage emitter electrodes and the low-voltage emitter electrodes is 0, the other n−4 electrodes serve as receiver electrodes, and a potential different between each group of attenuation-lowering remote detection emitter electrode group-receiver electrodes is recorded as a potential different for attenuation-lowering remote detection;
another metal electrode combination, never being selected, is selected as a attenuation-lowering remote emitter electrode group, the potential different between each group of attenuation-lowering remote emitter electrode group-receiver electrodes is measured until all possible metal electrode combinations are selected, and the potential different for attenuation-lowering remote detection is recorded.

the orientation pressure signal obtaining unit is configured to continuously obtain real-time pressure signals through all multidirectional pressure sensors;

the flowing state analyzing unit is configured in such a way that the single-monitoring-device electrical signal data and the real-time pressure signals are obtained by the ground monitoring device, and the real-time pressure signals are counted into a pressure signal set;

a latest pressure signal segment with a preset duration is intercepted, and the fluid flowing condition at the view of the pressure sensor is analyzed;

the single-monitoring-device electrical signal data is inverted to obtain resistivity grid distribution images in all the orientations, specifically, with inversion of the single-monitoring-device electrical signal data, the resistivity grid distribution images in one orientation, as shown in FIG. 5, is obtained firstly, and then the resistivity grid distribution images in all the orientations of the single monitoring apparatus, as shown in FIG. 6, are obtained by combining the resistivity grid distribution images; and orientation $CO_2$ distribution and the $CO_2$ flowing state at a view of an electrode are obtained based on the resistivity grid distribution images, wherein orientation $CO_2$ distribution is shown in FIG. 7, and the $CO_2$ flowing state at the view of the electrode may be obtained by fitting adjacent turns of $CO_2$ distribution.

Specifically, the fluid flowing condition at the view of the pressure sensor in a detection range from a corresponding depth horizontal direction to a wellbore is obtained through a latest pressure signal segment.

In this embodiments, the obtaining the fluid flowing condition at the view of the pressure sensor in the detection range from the corresponding depth horizontal direction to the wellbore through a latest pressure signal record comprises: drawing a double logarithmic curve based on the obtained latest pressure signal segment, selecting a correct model according to the geological conditions, and making typical curve fitting to obtain the fluid flowing state at the view of the pressure sensor; and specifically comprises: processing the latest pressure signal segment into pressure derivative data, and calculating a pressure drop derivative, $$\Delta' p_j = \left[\frac{\Delta(\Delta p)}{\Delta t}\right]_j = \frac{p_{j-1} - p_j}{t_j - t_{j-1}}$$

where $\Delta t$ represents an injection shut-in pressure drop time, $\Delta p$ represents an injection shut-in pressure drop value, and $\Delta' p_j$ represents a pressure drop derivative at the time j;

with $\Delta' p_j$ and $\Delta p$ as longitudinal coordinates and $\Delta t$ as a horizontal ordinate, drawing a double logarithmic curve for an actually measured pressure drop;

selecting a theoretical model, and drawing a pressure drop theoretical curve; and analyzing the fluid flowing state underground based on the pressure drop theoretical curve.

Figure 8:
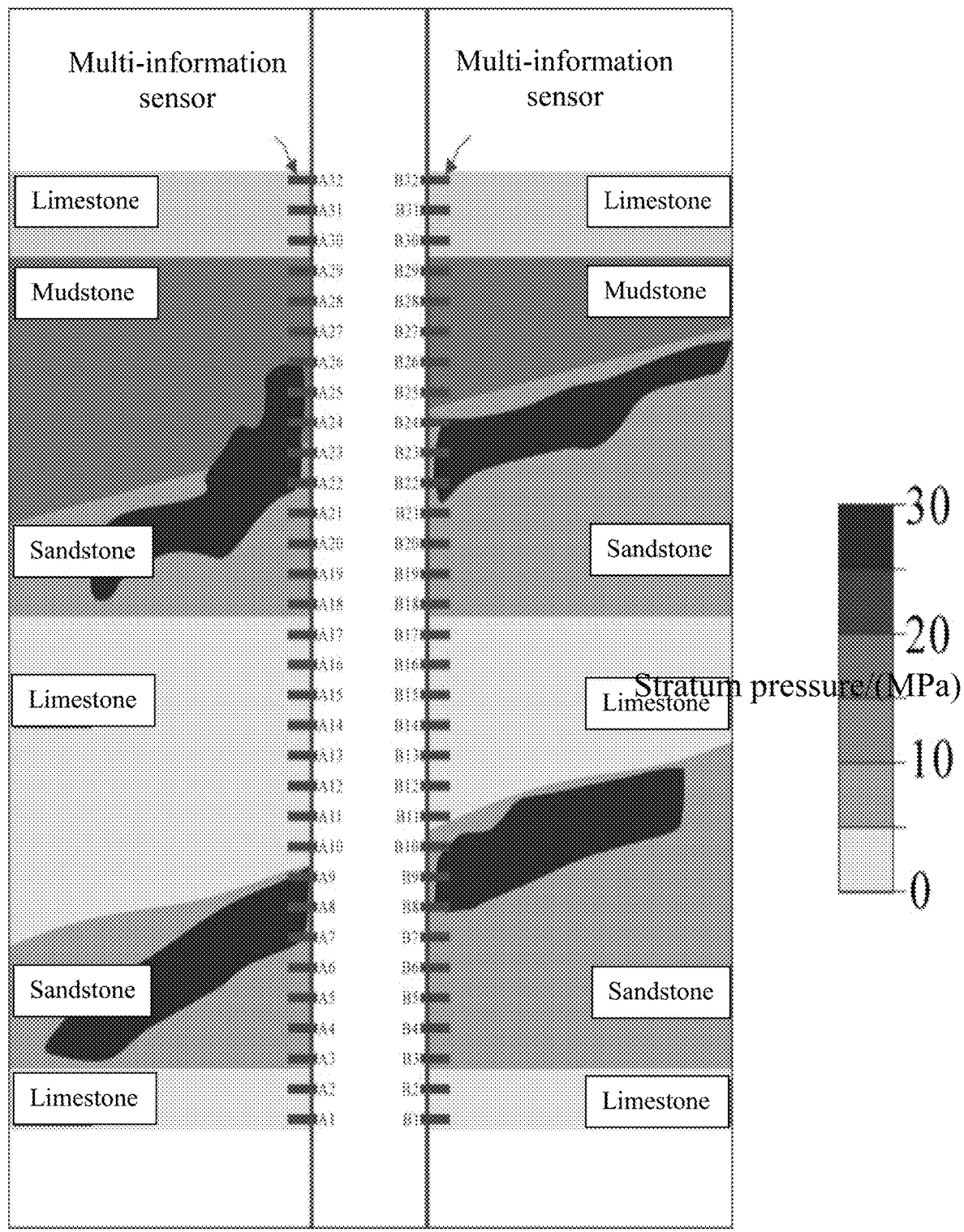
FIG. 8 is schematic diagram of a $CO_2$ flowing state at a pressure view in embodiments of the present invention.

The $CO_2$ flowing state at the pressure view is obtained based on the fluid flowing condition at the view of the pressure sensor and an orientation $CO_2$ distribution image. The $CO_2$ flowing state at the pressure view is prediction on a $CO_2$ flowing state at a next time on the basis of the $CO_2$ distribution image; and when the $CO_2$ flowing state at the pressure view abnormally varies, an electrode monitoring mode may be immediately enabled for precision confirmation. The $CO_2$ flowing state at the pressure view is as shown in FIG. 8. Compared with the orientation $CO_2$ distribution diagram 7 obtained only by the electrodes, for $CO_2$ flowing at the pressure view, the obtained recognition precision is greatly weakened; when $CO_2$ occurs in the detection range, the pressure sensors can obviously sense pressure increase in one geology, and $CO_2$ cannot cross over a boundary between different geologies under the condition without leaking, that is, the pressure sensors on the upper side of a boundary of one geology cannot be increased along with increase of the pressure sensors on the lower side of a boundary of one geology; and if a lot of pressures obtained by the pressure sensors in a vertical direction are increased, particularly, the pressures obtained by the pressure sensors over the boundary between different geologies are increased, it shows that there may a $CO_2$ leakage condition.

In this embodiment, a specific obtaining mode of the $CO_2$ flowing state at the pressure view comprises: a relationship is established between the fluid flowing condition at the view of the pressure sensor and the orientation $CO_2$ distribution image, the orientation $CO_2$ distribution image is taken as a standard label of the fluid flowing condition at the view of the pressure sensor, and a $CO_2$ flowing state prediction neural network at the pressure view is obtained by training; the $CO_2$ flowing state prediction neural network at the pressure view may employ a model similar to water flow prediction; and as for each turn of obtained fluid flowing condition at the view of the pressure sensor, the $CO_2$ flowing state at the pressure view is predicted by the trained $CO_2$ flowing state prediction neural network at the pressure view to achieve continuous monitoring, the current $CO_2$ flowing state at the pressure view is replaced when orientation $CO_2$ distribution in each turn is obtained, and prediction at the next time is conducted from the current $CO_2$ flowing state at the pressure view. In addition, as ranges of the obtained resistivity grid distribution images are relatively close to each other when monitoring is conducted purely depending on the electrodes, when monitoring achieves a certain distance, the precision is easily weakened; whereas with detection with the pressure sensor, electrode detection may be supplemented, and then the arrangement density of the monitoring devices may be lowered.

In order to avoid interference and improvement on detection precision, each orientation electrode array of the present invention can only obtain orientation electrical signals in single orientation each time, so that there is an interval blank period between the obtained orientation electrical signals in various orientations, resistivity grid distribution variation data in a short time may be predicted through the underground fluid flowing state, and continuous detection is achieved.

By combining the detection characteristics of the pressure sensors and range electrodes, this embodiment further achieves accurate detection on $CO_2$ storage state under different geological conditions of flowing in sandstone reservoirs, leakage in mudstones and leakage in mudstone caprocks.

In this embodiment, the obtaining the resistivity grid distribution images and the resistivity grid variation data by inverting the latest pressure signal segment and the orientation electric signal data further comprises: calculating an estimated pressure variation quantity of $CO_2$ entering a corresponding detection region based on different rock strata where the pressure sensors arc located and different geological conditions; and judging whether there is a $CO_2$ longitudinal flow or not by comparing the latest pressure signal segment with the estimated pressure variation quantity.

Figure 9:
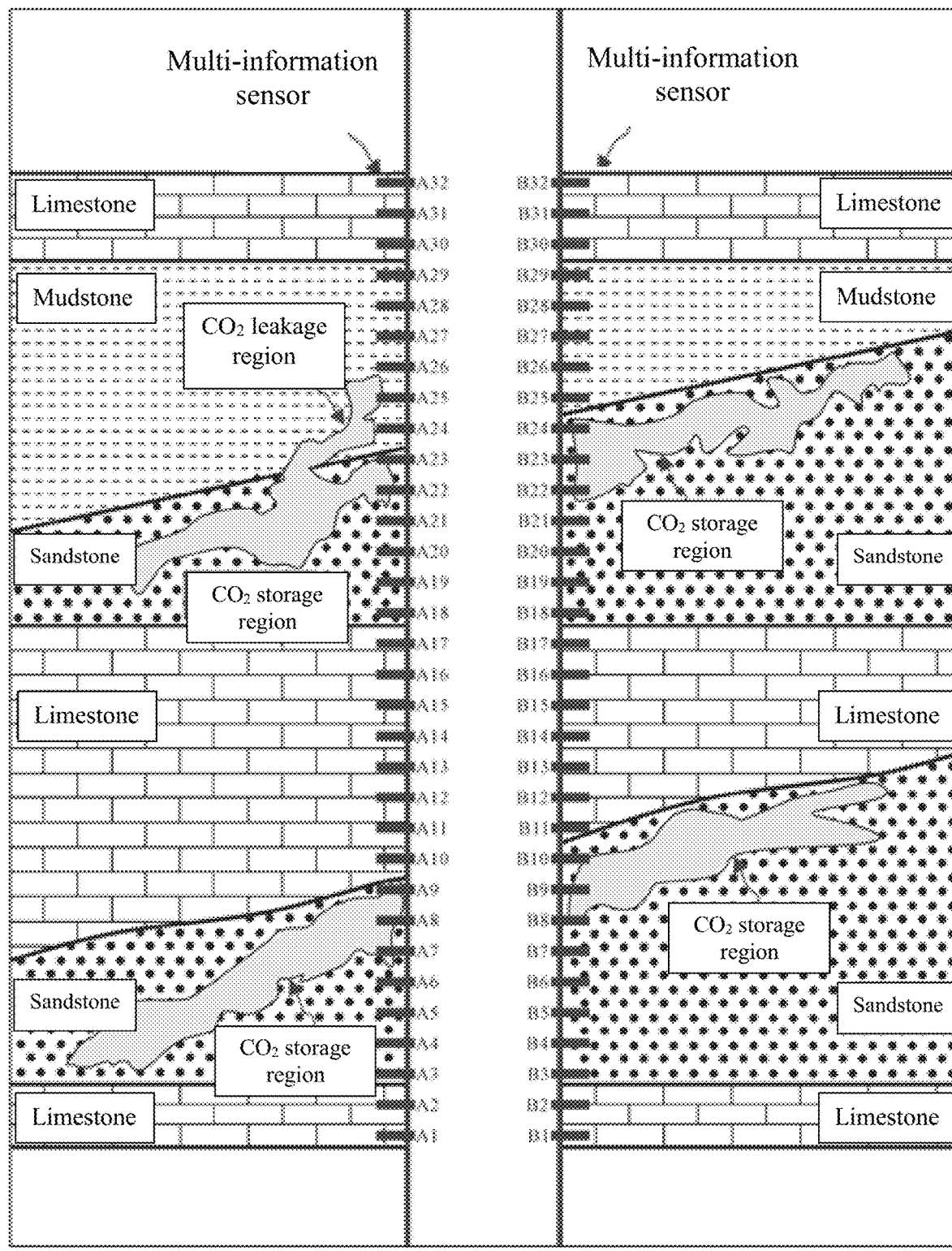
FIG. 9 is distribution schematic diagram of $CO_2$ in geology of a single monitoring apparatus in embodiments of the present invention.

The flowing component analyzing unit is configured to calculate orientation $CO_2$ distribution and a $CO_2$ flowing state at an electrode view based on the resistivity grid distribution images, and the $CO_2$ flowing state at the electrode view is shown in FIG. 9. In FIG. 9, it shows $CO_2$ distribution under two conditions of $CO_2$ leakage and normal storage; during normal storage, $CO_2$ is irregularly distributed, but rarely crosses over a boundary between different geologies; and when $CO_2$ crosses over the boundary between the geologies, $CO_2$ leakage is considered occurring, so that it is very important to accurately obtain the boundary of $CO_2$ underground.

The regional $CO_2$ state analyzing unit is configured to summarize the $CO_2$ flowing states at the electrode view and the $CO_2$ flowing states at the pressure view of all the $CO_2$ underground monitoring apparatuses to obtain the $CO_2$ flowing state between devices and
obtain the $CO_2$ regional storage state based on the $CO_2$ flowing state between devices.

In this embodiment, the obtaining the $CO_2$ regional storage state based on the $CO_2$ flowing state at the electrode view and the $CO_2$ flowing state between devices is specifically as follows:
the $CO_2$ flowing state between the devices is analyzed; and if the $CO_2$ flowing state of a certain probing station represents that there is $CO_2$ leakage in the detection region, orientation pressure may be reduced in probing stations in upstream and downstream directions of the detection region, and the $CO_2$ flowing state of the probing station in each direction may display that $CO_2$ moves in a leakage direction. The present invention may verify whether $CO_2$ leakage indeed occurs or not in the corresponding detection region of the probing station through the $CO_2$ flowing state between the devices and may further conduct fuzzy monitoring through the $CO_2$ flowing state between the devices when a certain station is maintained or damaged. This embodiment conducts complementary analysis by obtaining data of two different attributes of electricity and pressure at the same time and may further conduct analysis by singly using one attribute at the same time, so that the reliability of monitoring is improved.

The continuous monitoring unit is configured to repeat functions of the orientation electrical signal obtaining unit, the orientation pressure signal obtaining unit, the flowing state analyzing unit, the flowing component analyzing unit and the regional $CO_2$ state analyzing unit and continuously monitor the $CO_2$ flowing state in the region underground.

Figure 2:
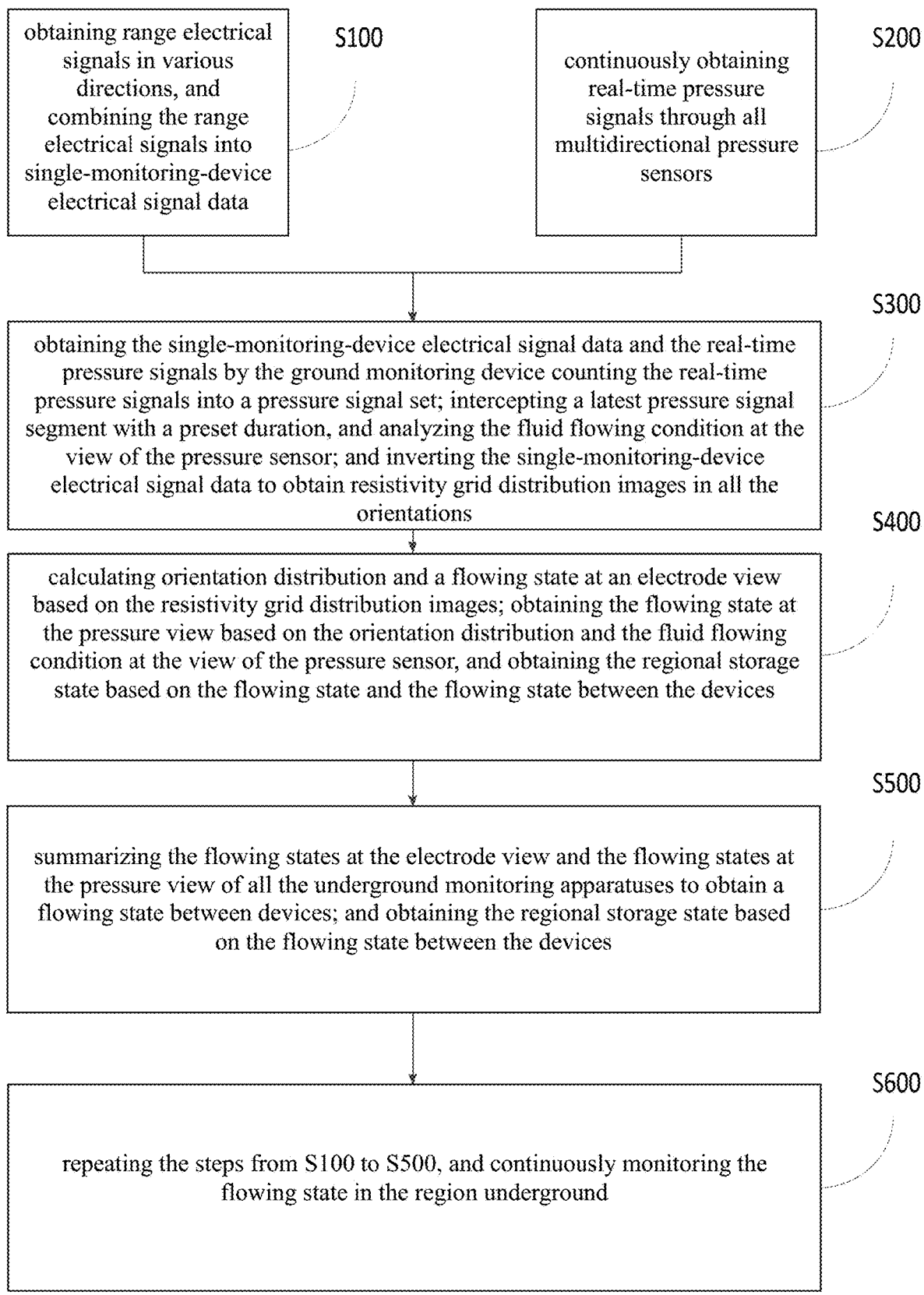
FIG. 2 is a flow chart of a $CO_2$ storage state networking monitoring method with multi-information fusion according to embodiments of the present invention.

A $CO_2$ storage state networking monitoring method with multi-information fusion of the third embodiment of the present invention is shown in FIG. 2. The method comprises:
step S100, selecting a single multi-information sensor array through the ground monitoring device, providing an emitter electrode and a receiver electrode, emitting a detection current in a preset waveform by the emitter electrode, receiving the lost detection current by the receiver electrode, obtaining a potential difference between the electrodes, measuring the potential difference between the electrodes by selecting another combination of the emitter electrode and the receiver electrode, enabling all the potential differences between the electrodes in one orientation to form orientation electrical signal data, obtaining electrical signal data in the another orientation by selecting another orientation electrode array until collection of all the electrical signal data in all orientations of single monitoring device is completed, and combining all the orientation electrical signal data into single-monitoring-device electrical signal data;

step S200, continuously obtaining real-time pressure signals through all multidirectional pressure sensors;

step S300, obtaining the single-monitoring-device electrical signal data and the real-time pressure signals by the ground monitoring device, and counting the real-time pressure signals into a pressure signal set;

intercepting a latest pressure signal segment with a preset duration, and analyzing the fluid flowing condition at the view of the pressure sensor;

inverting the single-monitoring-device electrical signal data to obtain resistivity grid distribution images in all the orientations;

step S400, calculating orientation $CO_2$ distribution and a $CO_2$ flowing state at an electrode view based on the resistivity grid distribution images;

obtaining the $CO_2$ flowing state at the pressure view based on the orientation $CO_2$ distribution and the fluid flowing condition at the view of the pressure sensor, and obtaining the $CO_2$ regional storage state based on the $CO_2$ flowing state and the $CO_2$ flowing state between the devices;

step S500, summarizing the $CO_2$ flowing states at the electrode view and the $CO_2$ flowing states at the pressure view of all the $CO_2$ underground monitoring apparatuses to obtain a $CO_2$ flowing state between devices;

obtaining the $CO_2$ regional storage state based on the $CO_2$ flowing state between devices;

step S600, repeating the steps from S100 to S500, and continuously monitoring the $CO_2$ flowing state in the region underground.

An electronic device of the fourth embodiment of the present invention, comprising at least one processor and a memory in communication connection with the at least one processor, wherein the memory stores instructions which may be executed by the processor, and the instructions are used for being executed by the processor so as to implement the $CO_2$ storage state networking monitoring method with multi-information fusion.

A computer center control readable storage medium of the fifth embodiment of the present invention, wherein the computer center control instructions are executed by a computer center control to implement the $CO_2$ storage state networking monitoring method with multi-information fusion

The invention claimed is:

1. A $CO_2$ storage state networking monitoring device with multi-information fusion, characterized by comprising a plurality of dispersed multi-information $CO_2$ underground monitoring devices and a ground monitoring device;
each of the multi-information $CO_2$ underground monitoring device comprises a cable mounted at the external of a non-conductive sleeve and a preset number of multi-information sensor arrays in preset orientations; and each sensor terminal of each multi-information sensor array at least comprises orientation electrodes and a pressure sensor and is connected with the cable,
wherein each multi-information sensor array comprises a preset number of orientation electrodes which are in one orientation and vertically inserted into the non-conductive sleeve; and the pressure sensor is a multi-directional sensor;

the ground monitoring device comprises a current source, an emitting apparatus, a downhole sensor detection module and a computer center control;

the monitoring system comprises an orientation electrical signal obtaining unit, an orientation pressure signal obtaining unit, a flowing state analyzing unit, a flowing component analyzing unit, a regional $CO_2$ state analyzing unit and a continuous monitoring unit;

the orientation electrical signal obtaining unit is configured in such a way that a single multi-information sensor array is selected through the ground monitoring device, an emitter electrode and a receiver electrode are provided, a detection current in a preset waveform is emitted by the emitter electrode, the lost detection current is received by the receiver electrode, a potential difference between the electrodes is obtained, the potential difference between the electrodes is measured by selecting another combination of the emitter electrode and the receiver electrode, all the potential differences between the electrodes in one orientation form orientation electrical signal data, electrical signal data in the another orientation is obtained by selecting another orientation electrode array until collection of all the electrical signal data in all orientations of single monitoring device is completed, and all the orientation electrical signal data is combined into single-monitoring-device electrical signal data;

the orientation pressure signal obtaining unit is configured to continuously obtain real-time pressure signals through all multidirectional pressure sensors;

the flowing state analyzing unit is configured in such a way that the single-monitoring-device electrical signal data and the real-time pressure signals are obtained by the ground monitoring device, and the real-time pressure signals are counted into a pressure signal set;

a latest pressure signal segment with a preset duration is intercepted, and the fluid flowing condition at the view of the pressure sensor is analyzed;

the single-monitoring-device electrical signal data is inverted to obtain resistivity grid distribution images in all the orientations;

the flowing component analyzing unit is configured to calculate orientation $CO_2$ distribution and a $CO_2$ flowing state at an electrode view based on the resistivity grid distribution images;

a $CO_2$ flowing state at a pressure view is obtained based on orientation $CO_2$ distribution and a fluid flowing condition at a view of a pressure sensor;

the regional $CO_2$ state analyzing unit is configured to summarize the $CO_2$ flowing states at the electrode view and the $CO_2$ flowing states at the pressure view of all the $CO_2$ underground monitoring apparatuses to obtain a $CO_2$ flowing state between the plurality of dispersed multi-information $CO_2$ underground monitoring devices and obtain the $CO_2$ regional storage state based on the $CO_2$ flowing state between the plurality of dispersed multi-information $CO_2$ underground monitoring devices;

the continuous monitoring unit is configured to repeat functions of the orientation electrical signal obtaining unit, the orientation pressure signal obtaining unit, the flowing state analyzing unit, the flowing component analyzing unit and the regional $CO_2$ state analyzing unit and continuously monitor the $CO_2$ flowing state in the region underground.

2. The $CO_2$ storage state networking monitoring system with multi-information fusion according to claim 1, characterized in that a running mode of the orientation electrical signal obtaining unit comprises a single-electrode emitting measurement mode, a symmetric-electrode emitting measurement mode, a remote detection mode and an attenuation-lowering remote detection mode;

the single-electrode emitting measurement mode is follows:

any one metal electrode is selected as the emitter electrode, the other n−1 electrodes serve as the receiver electrodes, the potential difference between the electrodes in each group of emitter electrode-receiver electrodes is recorded as a potential difference for single-electrode emitting measurement;

another metal electrode, never being selected, is selected as the emitter electrode, the potential difference between the electrodes in each group of emitter electrode-receiver electrodes is measured until all the metal electrodes have been selected as the emitter electrodes, and the potential difference for single-electrode emitting measurement is recorded;

the symmetric-electrode emitting measurement mode is follows:

the center of a length of each non-conductive sleeve is selected as a symmetric axis, and the metal electrodes, equally distant from the symmetric axis, serve as a metal electrode pair;

any one metal electrode pair is selected as the emitter electrode pair, the other n−2 electrodes serve as the receiver electrodes, the potential difference between the electrodes in each group of the emitter electrode pair-receiver electrodes is recorded as a potential difference for symmetric-electrode emitting measurement;

another metal electrode pair, never being selected, is selected as the emitter electrode, the potential difference between the electrodes in each group of emitter electrode-receiver electrodes is measured until all the metal electrode pairs have been selected as the emitter electrode pairs, and the potential difference for symmetric-electrode emitting measurement is recorded;

the remote detection mode is as follows:

two electrodes A and B at a preset interval of k electrodes are selected as high-voltage emitter electrodes, wherein k is even;

two electrodes C and D in the middle between the electrodes A and B are selected as high-voltage emitter electrodes, and A, B, C and D form a high-voltage emitter electrode group;

a detection current at high voltage is emitted by the high-voltage emitter electrodes, the other n−4 electrodes serve as receiver electrodes, and the potential difference between each group of high-voltage emitter electrode group-receiver electrodes is recorded as a potential difference for remote detection;

another metal electrode combination, never being selected, is selected as a high-voltage emitter electrode group, the potential difference between each group of high-voltage emitter electrode group-receiver electrodes is measured until all possible high-voltage metal electrode combinations are selected, and the potential difference for remote detection is recorded;

the attenuation-lowering remote detection mode is as follows:

two electrodes E and F at a preset interval of q electrodes are selected as low-voltage emitter electrodes, wherein q is even;

two electrodes G and H in the middle between the electrodes E and F are selected as high-voltage emitter electrodes, and E, F, G and H serve as an attenuation-lowering remote detection emitter electrode group;

a detection current at low voltage is emitted by the low-voltage emitter electrodes, a detection current at high voltage is emitted by the high-voltage emitter electrodes, at this time, the potential difference between the two electrodes, close to the low-voltage emitter electrodes between high-voltage emitter electrodes and the low-voltage emitter electrodes is 0, the other n−4 electrodes serve as receiver electrodes, and the potential difference between each group of attenuation-lowering remote detection emitter electrode group-receiver electrodes is recorded as a potential difference for attenuation-lowering remote detection;

another metal electrode combination, never being selected, is selected as a attenuation-lowering remote emitter electrode group, the potential difference between each group of attenuation-lowering remote emitter electrode group-receiver electrodes is measured until all possible metal electrode combinations are selected, and the potential difference for attenuation-lowering remote detection is recorded.

3. The $CO_2$ storage state networking monitoring system with multi-information fusion according to claim 2, characterized in that the obtaining the fluid flowing condition at the view of the pressure sensor in the detection range from the corresponding depth horizontal direction to the wellbore through the latest pressure signal segment comprises: drawing a double logarithmic curve based on the obtained latest pressure signal segment, selecting a correct model according to the geological conditions, and making typical curve fitting to obtain the fluid flowing condition at the view of the pressure sensor.

4. The $CO_2$ storage state networking monitoring system with multi-information fusion according to claim 2, characterized in that the obtaining the $CO_2$ flowing state at the pressure view based on the fluid flowing condition at the view of the pressure sensor and the orientation $CO_2$ distribution image further comprises: calculating an estimated pressure variation quantity of $CO_2$ entering a corresponding detection region based on different rock strata where the pressure sensors are located and different geological conditions; and judging whether there is a $CO_2$ longitudinal flow or not by comparing the latest pressure signal segment with the estimated pressure variation quantity.

5. The $CO_2$ storage state networking monitoring system with multi-information fusion according to claim 1, characterized in that a $CO_2$ flowing state at a pressure view is obtained based on orientation $CO_2$ distribution and a fluid flowing condition at a view of a pressure sensor;

the fluid flowing condition at the view of the pressure sensor in a detection range from a corresponding depth horizontal direction to a wellbore is obtained through a latest pressure signal segment;

the $CO_2$ flowing state at the pressure view is obtained based on the fluid flowing condition at the view of the pressure sensor and an orientation $CO_2$ distribution image.

6. The $CO_2$ storage state networking monitoring system with multi-information fusion according to claim 1, characterized in that a $CO_2$ regional storage state is obtained based on the $CO_2$ flowing state and a $CO_2$ flowing state between the plurality of dispersed multi-information $CO_2$ underground monitoring devices;

the $CO_2$ flowing state between the plurality of dispersed multi-information $CO_2$ underground monitoring devices is analyzed; and if the $CO_2$ flowing state of a certain monitoring device represents that there is $CO_2$ leakage in the detection region, orientation pressure may be reduced in probing stations in upstream and downstream directions of the detection region, and the $CO_2$ flowing state of the probing station in each direction may display that $CO_2$ moves in a leakage direction.

7. An electronic device, comprising at least one processor and a memory in communication connection with the at least one processor, wherein the memory stores instructions which may be executed by the processor, and the instructions are used for being executed by the processor so as to implement the $CO_2$ storage state networking monitoring method with multi-information fusion according to claim 6.

8. A $CO_2$ storage state networking monitoring method with multi-information fusion, characterized in that the method is applied to the $CO_2$ storage state networking monitoring device with multi-information fusion, comprising a plurality of dispersed multi-information $CO_2$ underground monitoring devices and a ground monitoring device;

each of the multi-information $CO_2$ underground monitoring device comprises a cable mounted at the external of a non-conductive sleeve and a preset number of multi-information sensor arrays in preset orientations; and each sensor terminal of each multi-information sensor array at least comprises orientation electrodes and a pressure sensor and is connected with the cable;

wherein each multi-information sensor array comprises a preset number of orientation electrodes which are in one orientation and vertically inserted into the non-conductive sleeve; and the pressure sensor is a multi-directional sensor;

the ground monitoring device comprises a current source, an emitting apparatus, a downhole sensor detection module and a computer center control;

comprises:

step S100, selecting a single multi-information sensor array through the ground monitoring device, providing an emitter electrode and a receiver electrode, emitting a detection current in a preset waveform by the emitter electrode, receiving the lost detection current by the receiver electrode, obtaining a potential difference between the electrodes, measuring the potential difference between the electrodes by selecting another combination of the emitter electrode and the receiver electrode, enabling all the potential differences between the electrodes in one orientation to form orientation electrical signal data, obtaining electrical signal data in the another orientation by selecting another orientation electrode array until collection of all the electrical signal data in all orientations of single monitoring device is completed, and combining all the orientation electrical signal data into single-monitoring-device electrical signal data;

step S200, continuously obtaining real-time pressure signals through all multidirectional pressure sensors;

step S300, obtaining the single-monitoring-device electrical signal data and the real-time pressure signals by the ground monitoring device, and counting the real-time pressure signals into a pressure signal set;

intercepting a latest pressure signal segment with a preset duration, and analyzing the fluid flowing condition at the view of the pressure sensor;

inverting the single-monitoring-device electrical signal data to obtain resistivity grid distribution images in all the orientations;

step S400, calculating orientation $CO_2$ distribution and a $CO_2$ flowing state at an electrode view based on the resistivity grid distribution images;

obtaining the $CO_2$ flowing state at the pressure view based on the orientation $CO_2$ distribution and the fluid flowing condition at the view of the pressure sensor, and obtaining the $CO_2$ regional storage state based on the $CO_2$ flowing state and the $CO_2$ flowing state between the plurality of dispersed multi-information $CO_2$ underground monitoring devices;

step S500, summarizing the $CO_2$ flowing states at the electrode view and the $CO_2$ flowing states at the pressure view of all the $CO_2$ underground monitoring apparatuses to obtain a $CO_2$ flowing state between the plurality of dispersed multi-information $CO_2$ underground monitoring devices;

obtaining the $CO_2$ regional storage state based on the $CO_2$ flowing state between the plurality of dispersed multi-information $CO_2$ underground monitoring devices;

step S600, repeating the steps from S100 to S500, and continuously monitoring the $CO_2$ flowing state in the region underground.

\* \* \* \* \*